United States Patent [19]
Gonzalez

[11] Patent Number: 5,308,328
[45] Date of Patent: May 3, 1994

[54] SINGLE-USE SYRINGE

[76] Inventor: Antonio S. Gonzalez, Canyoles 6., 46900 El Vedat De Torrent (Valencia), Sweden

[21] Appl. No.: 838,417
[22] PCT Filed: Jul. 25, 1991
[86] PCT No.: PCT/ES91/00047
§ 371 Date: Mar. 9, 1992
§ 102(e) Date: Mar. 9, 1992
[87] PCT Pub. No.: WO92/01486
PCT Pub. Date: Feb. 6, 1992

[30] Foreign Application Priority Data
Jul. 25, 1990 [SE] Sweden .............................. 9002007

[51] Int. Cl.⁵ .................................................. A61M 5/00
[52] U.S. Cl. .................................. 604/110; 604/218
[58] Field of Search ........................ 604/110, 187, 218

[56] References Cited
FOREIGN PATENT DOCUMENTS
9007949 1/1989 World Int. Prop. O. .......... 604/110

Primary Examiner—John D. Yasko
Attorney, Agent, or Firm—Mason, Kolehmainen, Rathburn & Wyss

[57] ABSTRACT

The syringe is comprised of an external cylindrical body (1) and a suction and ejection piston (2) displaceable within said body, the piston including at its internal end the corresponding seal (3). According to the invention, said seal is held at the extremity of the piston by means of one of a plurality of arms (4) hinged at said end of the piston, said arm or arms traversing the side wall of the seal to retain the latter. The arms have a sharpened free end (6) and a cutting front edge (7), so that, during the advance movement of the piston during the ejection phase, the wall of the external cylindrical body is cut, no cut being done during the suction displacement. The syringe is disposable and not reusable after its first and single use.

2 Claims, 1 Drawing Sheet

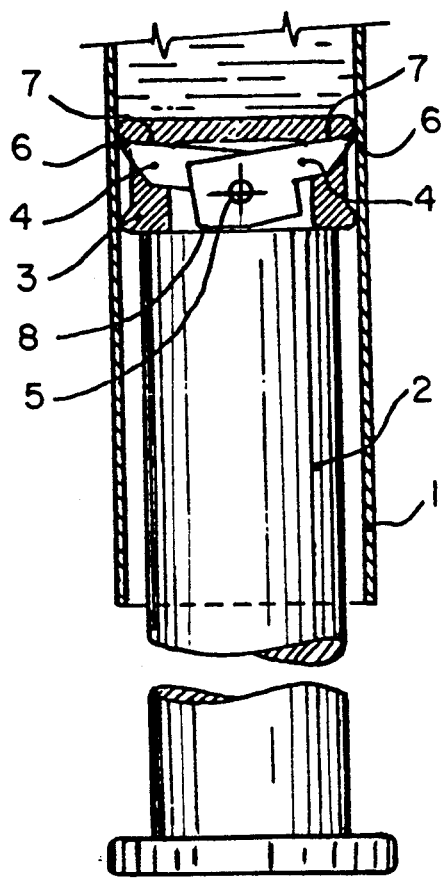
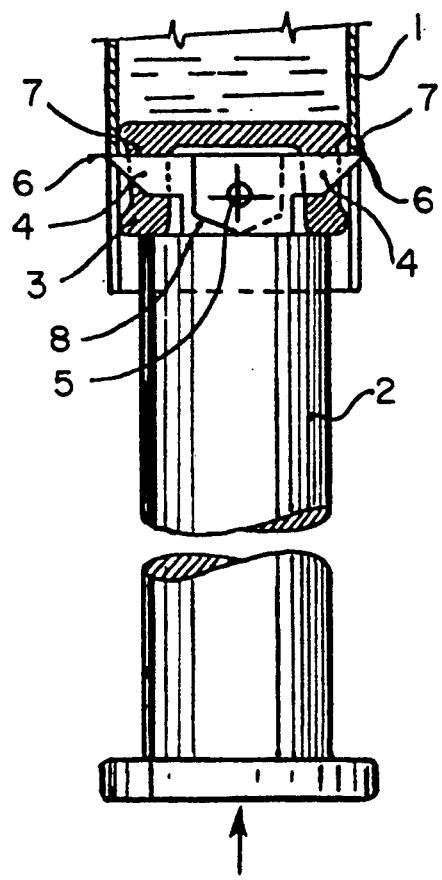
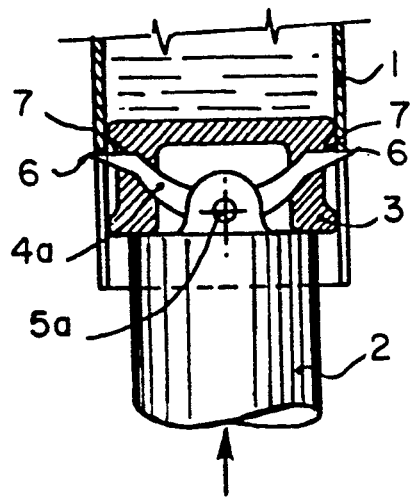

SINGLE-USE SYRINGE

The invention refers to a disposable or single-use syringe, the structure of which is such that after it has been used once it is impossible to use it again.

At the present time a number of single-use or disposable syringes are known, and which are used by medical staff both for giving injections and for extracting blood, or other similar uses.

The use of disposable or single-use syringes is a general practice in order to prevent all kinds of contagions, and this is becoming widespread among those persons addicted to drugs, in which case a single syringe is used several times over and even by several people, with the subsequent risk of contracting certain illnesses, ranging from the normal or typical hepatitis to the serious and fatal AIDS.

Undoubtedly there are syringes that have been constructed in such a way as to make re-use difficult, although in all cases they can be, and indeed are, tampered with and adapted by drug addicts so that they can be used again.

The syringe put forward here has been designed and conceived in such a way that, once it has been used, there is no possibility of its being used again as, on the one hand, a single use results in the cylinder no longer being usable and, on the other hand, tampering with the syringe in order to try to re-use the piston results in the end itself or the seal provided at the end of the piston being unusable. The syringe therefore cannot be used more than once even should an attempt be made to tamper with it.

To be exact, the syringe put forward is made up, in the conventional way, of a cylinder with a piston that moves up and down the cylinder. At the free end of the piston there is a seal to ensure that the liquid is drawn in correctly, as well as to inject the liquid previously drawn in. On the basis of this structure, the syringe in question shows the particular feature of the seal at the end of the piston being attached to the latter by means of one or more radial arms provided at the end of the piston, and which are hinged at the point of attachment or assembly in such a way that, during suction, the arm or arms can slide along the inside surface of the external cylindrical body whereas, during the impulse movement, the arm or arms, which have a pointed end and a sharpened or cutting section, produce a piercing action with the subsequent cutting of the cylindrical body during the impulse movement of the piston. In this way, the external cylindrical body is rendered useless after the syringe has been used for the first time. Should an attempt be made to tamper with the syringe in order to use it again, the only thing that can be done is to dismantle the cutting arm or arms but this involves dismantling the seal, which could no longer be attached to the piston since this must be done precisely by means of the aforementioned cutting arm or arms.

So as to make it easier to understand the features of this invention, there follows a detailed description on the basis of a set of drawings attached to the description, forming an integral part of the same, and in which the following has been depicted merely as a guide and in a non-restrictive way.

FIG. 1 shows a sectional view of the part of the syringe to which the improvement has been added, and corresponds to the syringe's absorption or suction stage during which the cutting arms are partially brought in and can slide along the inside of the external cylindrical body without the latter suffering any damage.

FIG. 2 is the same drawing as FIG. 1 but showing the impulse or ejection movement, with the cutting arms severing the external cylindrical body as the piston advances.

FIG. 3 shows another, similar view but with a different cutting-arm shape, the arms in this case being made up of a single-piece body with two opposing sections.

As can be seen in these figures, and in particular the first two, the syringe in question comprises the standard external cylindrical body (1) and the piston (2) which moves along the inside of the body (1). To the inside end of the piston is fitted the corresponding seal (3) which allows suction and ejection to take place.

As a means for holding the seal firm (3), two radial arms (4) are fitted to the end of the piston (2) and are centrally hinged on a common axis (5). The number of arms may vary from one to three, four or even more. At any event, the free ends of these arms (4) are pointed (6) and bevelled (8) on the rear edges, while the end sections (7) of the front edges are sharpened, thereby forming on each arm (4) a blade which performs no cutting action whatsoever when the piston moves in a backward direction (suction stage), whereas during ejection the pointed ends of these arms (4) pierce the cylinder (1) and the end cutting sections (7) sever the said cylindrical body (1).

The aforementioned arms (4) pass through the side wall of the seal (3), thereby fixing or securing the latter to the end of the piston (2), as these arms (4) are hinged precisely at the end of the said piston.

In an alternative system, as shown in FIG. 3, the arms (4) are made up of a single body (4a) constructed in tempered metal, with two opposing and fixed sections one on each side of a central hinge (5a) forming part of this body (4a), in such a way that these two sections are provided with the corresponding pointed end (6) and cutting end section (7) in the same manner as in the system described previously.

I claim:

1. A single-use syringe having a cylindrical body, piston means mounted in said body and movable along a longitudinal central axis therein in a respective fluid suction stroke and an opposite fluid ejection stroke seal means adjacent one end of the said piston means for fluid sealing between said body and said piston means, one or more cutting arms mounted adjacent said one end of said piston means for pivotal movement about one or more pivot axes transverse to said longitudinal axis between a retracted position when said piston means is moved on a suction stroke in said body and a cutting position when said piston means is moved on an ejection stroke for cutting an opening in a wall portion of said body, said pivot axes being in a fixed position relative to said piston means each said cutting arm having a pointed free end portions passing through a side portion of said seal means firmly securing said arm against pivotal movement penetrating said body during a suction stroke, each of said arms having a bevelled, stop surface engaging said piston means to prevent pivotal movement in one direction for allowing said arms to move along the inside of said cylindrical body during a stroke without cutting suction action, each of said arms having a sharpened front edge end section forming a cutting blade which is pivoted to a cutting position as said piston means moves on an ejection stroke inside of said cylindrical body to penetrate and cut through said wall of the said cylindrical body rendering said syringe unusable for further use after said ejection stroke is stopped.

2. The single-use syringe of claim 1, including more than one of said cutting arms formed by a single-piece element pivotally supported in the middle thereof.

* * * * *